United States Patent
Kobayashi et al.

(10) Patent No.: US 6,686,949 B2
(45) Date of Patent: Feb. 3, 2004

(54) ELECTRONIC ENDOSCOPE SYSTEM

(75) Inventors: Hiroyuki Kobayashi, Tokyo (JP); Hideo Sugimoto, Tokyo (JP); Kohei Iketani, Saitama (JP)

(73) Assignee: Pentax Corporation, Tokyo (JP)

( * ) Notice: Subject to any disclaimer, the term of this patent is extended or adjusted under 35 U.S.C. 154(b) by 427 days.

(21) Appl. No.: 09/758,180

(22) Filed: Jan. 12, 2001

(65) Prior Publication Data

US 2001/0008414 A1 Jul. 19, 2001

(30) Foreign Application Priority Data

Jan. 14, 2000 (JP) ..................... P2000-006919

(51) Int. Cl.$^7$ .............. H04N 9/47; A61B 1/04
(52) U.S. Cl. ............ 348/65; 348/72; 600/101
(58) Field of Search ............... 348/65, 71, 72, 348/74; 600/101, 103, 109, 118; A61B 1/04, 1/06; H04N 9/47

(56) References Cited

U.S. PATENT DOCUMENTS

| | | | | |
|---|---|---|---|---|
| 4,058,826 A | * | 11/1977 | Schneider | 348/184 |
| 5,051,776 A | * | 9/1991 | Mancino | 355/77 |
| 5,319,287 A | * | 6/1994 | Furukawa | 315/397 |
| 5,740,801 A | * | 4/1998 | Branson | 600/407 |
| 5,877,819 A | * | 3/1999 | Branson | 348/701 |
| 6,128,078 A | * | 10/2000 | Fateley | 356/330 |
| 6,527,716 B1 | * | 3/2003 | Eppstein | 600/309 |

* cited by examiner

*Primary Examiner*—Nhon Diep
(74) *Attorney, Agent, or Firm*—Greenblum & Bernstein, P.L.C.

(57) ABSTRACT

In an electronic endoscope system, a scope has a solid-state image sensor provided at a distal end thereof to generate image-pixel signals. An image-signal processing unit produces a video signal based on the image-pixel signals. An alteration system alters a peak-to-peak level of a synchronizing-signal component of the video signal. A manual setting system operates the alteration system to perform the alteration of the level of the synchronizing-signal component. An indicator system indicates the degree of alteration to the level of the synchronizing-signal component during the operation of the manual setting system.

14 Claims, 10 Drawing Sheets

ELECTRONIC ENDOSCOPE SYSTEM

BACKGROUND OF THE INVENTION

1. Field of the Invention

The present invention relates to an electronic endoscope system including a scope having a solid-state image sensor provided at a distal end thereof to generate image-pixel signals, an image-signal processing unit that produces a video signal on the basis of the image-pixel signals, and a TV monitor for reproducing and displaying an image in accordance with the video signal.

2. Description of the Related Art

In general, in such an electronic endoscope system, a component-type color video signal is produced on the basis of image-pixel signals obtained from a solid-state image sensor, such as a CCD (charge-coupled device) image sensor, to reproduce an image of high quality on a TV monitor. Usually, the component-type color video signal is composed of three-primary-color video signal components and a compound-synchronizing-signal component which includes various synchronizing signals, such as a horizontal synchronizing signal, a vertical synchronizing signal and so on.

As is well known, the compound-synchronizing-signal component is produced as a voltage signal, and the peak-to-peak level of the voltage signal is standardized to, for example, 4 volts. Thus, a medical TV monitor, used in the electronic endoscope system, is designed in accordance with the compound-synchronizing-signal component exhibiting the peak-to-peak level of 4 volts.

Since the medical TV monitor is expensive, a domestic TV monitor may be frequently substituted for the medical TV monitor. However, domestic TV monitors are not designed so as to accept the compound-synchronizing-signal component exhibiting the peak-to-peak level of 4 volts. Thus, the domestic monitors cannot properly function and display an image when being connected to an image-signal processing unit.

Specifically, after introducing an electronic endoscope system with a medical TV monitor into a medical facility, when the medical TV monitor is replaced by a domestic TV monitor, or when a domestic TV monitor is added to the introduced electronic endoscope system, a problem will occur.

SUMMARY OF THE INVENTION

Therefore, an object of the present invention is to provide an electronic endoscope system comprising a scope having a solid-state image sensor provided at a distal end thereof to generate image-pixel signals, and an image-signal processing unit that produces a video signal on the basis of the image-pixel signals, wherein a peak-to-peak level of the synchronizing-signal component of the video signal can be manually and easily altered such that various types of TV monitors can accept the video signal.

In accordance with the present invention, there is provided an electronic endoscope system including a scope having a solid-state image sensor provided at a distal end thereof to generate image-pixel signals, and an image-signal processing unit that produces a video signal based on the image-pixel signals. The electronic endoscope comprises, an alteration system that alters a peak-to-peak level of a synchronizing-signal component of the video signal, an manual setting system that manually operates the alteration system to perform the alteration of the peak-to-peak level of the synchronizing-signal component; an indicator system that indicates a degree of the alteration of the peak-to-peak level of the synchronizing-signal component during the operation of the manual setting system, and an output terminal that outputs the synchronizing-signal component having the peak-to-peak level defined by the alteration system.

Preferably, the manual setting system is provided in a housing of the image-signal processing unit so as to be accessible by a suitable manual tool.

The alteration system may comprise a voltage-controlled amplifier, an amplification factor of which is regulated in accordance with a level of a voltage signal applied thereto. In this case, the manual setting system may comprise a variable resistor that adjusts the level of the voltage signal.

The indicator system may include an indicator lamp visually provided at a suitable location of a housing of the image-signal processing unit, and a lamp driver system that controls lighting of the indicator lamp in accordance with the degree of alteration of the peak-to-peak level of the synchronizing-signal component. Preferably, the indicator lamp includes at least two light-emitting sources, and the driver system controls not only turn-ON and turn-OFF of the light-emitting sources but also brightness of the light-emitting sources in accordance with the degree of the alteration of the peak-to-peak level of the synchronizing-signal component. Also preferably, the respective light-emitting sources emit different monochromatic light.

The lamp driver system may include an ON/OFF switch element that controls supply of electrical power from the lamp driver system to the indicator lamp, and a timer system that turns OFF the ON/OFF switch element after a predetermined time is elapsed from a time at which the ON/OFF switch is turned ON.

Optionally, the lamp driver system may include a tool-detection system that detects whether access to the manual setting system by the manual tool is made, and the lamp driver system is allowed to feed electric power to the indicator lamp only when the access to the manual setting system by the manual tool is detected by the tool-detection system.

The lamp driver system may further include an ON/OFF switch element that controls the supply of the electrical power from the lamp driver system to the indicator lamp, and the ON/OFF switch is turned ON only when the access to the manual setting system by the manual tool is detected by the tool-detection system.

The manual setting system may include a portion which is manually operated by a suitable manual tool, and which is arranged such that the manual tool is operable without interfering with a signal cable extending from the output terminal.

BRIEF DESCRIPTION OF THE DRAWINGS

The object and other objects of the present invention will be better understood from the following descriptions, with reference to the accompanying drawings, in which.

DESCRIPTION OF THE PREFERRED EMBODIMENTS

Figure 1:
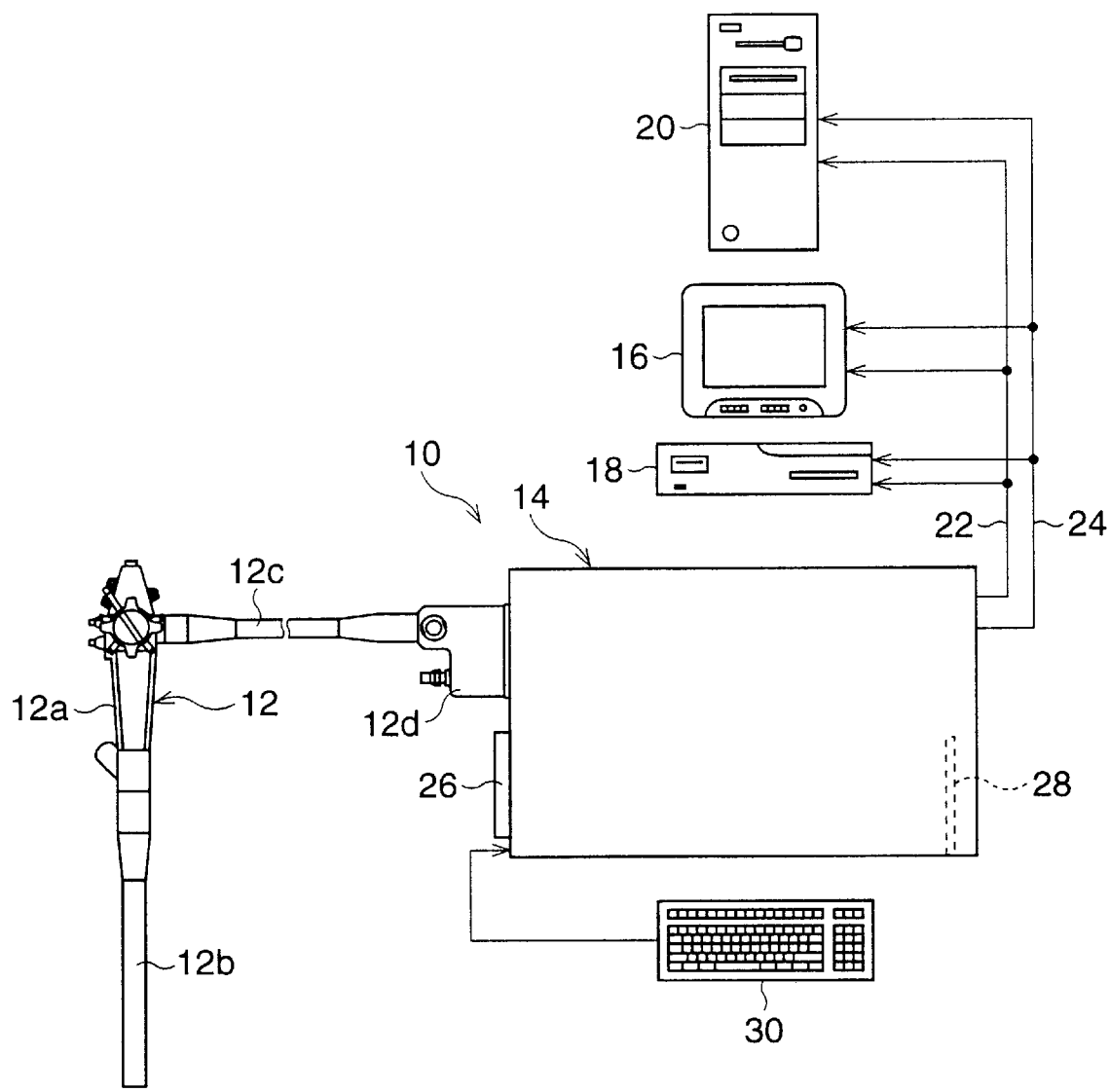
FIG. 1 is a schematic view showing an electronic endoscope system according to the present invention.

FIG. 1 schematically shows an electronic endoscope system, generally indicated by reference 10, according to the present invention. The electronic endoscope system 10 comprises an elongated scope 12 including a rigid conduit 12a, a flexible conduit 12b integrally formed with the rigid conduit 12a, and a flexible cable 12c extending from the rigid conduit 12a, with the flexible cable 12c terminating with a connector 12d. The electronic endoscope system 10 also comprises an image-signal processing unit 14 to which the scope 12 is detachably connected through the intermediary of the flexible cable 12c and the connector 12d. The scope 12 represents various types of scope, used for bronchial, esophageal, gastro, colon, etc. examinations, and these various types of scope use the image-signal processing unit 14 in common.

The flexible conduit 12b of the scope 12 has a solid-state image sensor (not shown), such as a CCD (charge-coupled-device) image sensor, at the distal end thereof, and the CCD image sensor is associated with an objective lens system (not shown). When the connection is established between the scope 12 and the image-signal processing unit 14, the CCD image sensor is electrically connected to an image-signal processor in the image-signal processing unit 14.

Also, the scope 12 includes a flexible optical light guide extended therethrough and formed from a bundle of optical fibers. The optical light guide terminates with a light-radiating end face at the distal end of the flexible conduit 12b of the scope 12, and is associated with a lighting lens system (not shown) provided thereat. When the connection is established between the scope 12 and the image-signal processing unit 14, the proximal end of the optical light guide is optically connected to a light source device provided in the image-signal processing unit 14, whereby the light, emitted from the light source device, radiates as an illuminating-light from the light-radiating end face of the optical light guide.

When the flexible conduit 12b of the scope 12 is inserted in the body of a patient, an illuminated object is focused as an optical image on a light-receiving surface of the CCD image sensor, by the associated objective lens system. The focused optical image is converted into analog image-pixel signals by the CCD image sensor, and the analog image-pixel signals are read from the CCD image sensor by a CCD driver provided in the connector 12d of the scope 12. The signals are then fed to the image-signal processor provided in the image-signal processing unit 14. In the image-signal processor, the image-pixel signals are suitably processed to produce a video signal, which is then fed to a TV monitor 16, thereby reproducing the object image on the TV monitor 16 in accordance with the video signal. Also, as shown in FIG. 1, the video signal may be fed to peripheral equipment, such as a video printer 18, an image-processing computer 20 and so on.

In this embodiment, to reproduce the image on the TV monitor 16 as a color image, an RGB field sequential-type color imaging method is incorporated in the electronic endoscope system. Thus, in the image-signal processor, the video signal is produced as a component-type color video signal, composed of red, green and blue video signal components, and a compound-synchronizing-signal component, which includes various synchronizing signals, such as a horizontal synchronizing signal, a vertical synchronizing signal and so on. In FIG. 1, a signal cable 22 is provided for feeding the red, green and blue video signal components, and a signal cable 24 is provided for feeding the compound-synchronizing-signal component, to the TV monitor 16 and other peripheral devices.

A front switch panel 26 is attached to a front wall of a housing of the image-signal processing unit 14, and various switches and indicator-lamps are mounted on the front switch panel 26. As shown by broken lines in FIG. 1, a circuit board 28 is provided in the housing of the image-signal processing unit 14, and has a voltage-level-regulating circuit for regulating an output voltage level (peak-to-peak level) of the compound-synchronizing-signal component. As stated in detail hereinafter, the voltage-level-regulating circuit includes an accessible adjuster, and, by using a suitable tool, such as a screw driver, such that the output voltage level of the compound-synchronizing-signal component can be manually regulated. Also, as shown in FIG. 1, a keyboard 30 is connected to the image-signal processing unit 14 as an input device.

Figure 2:
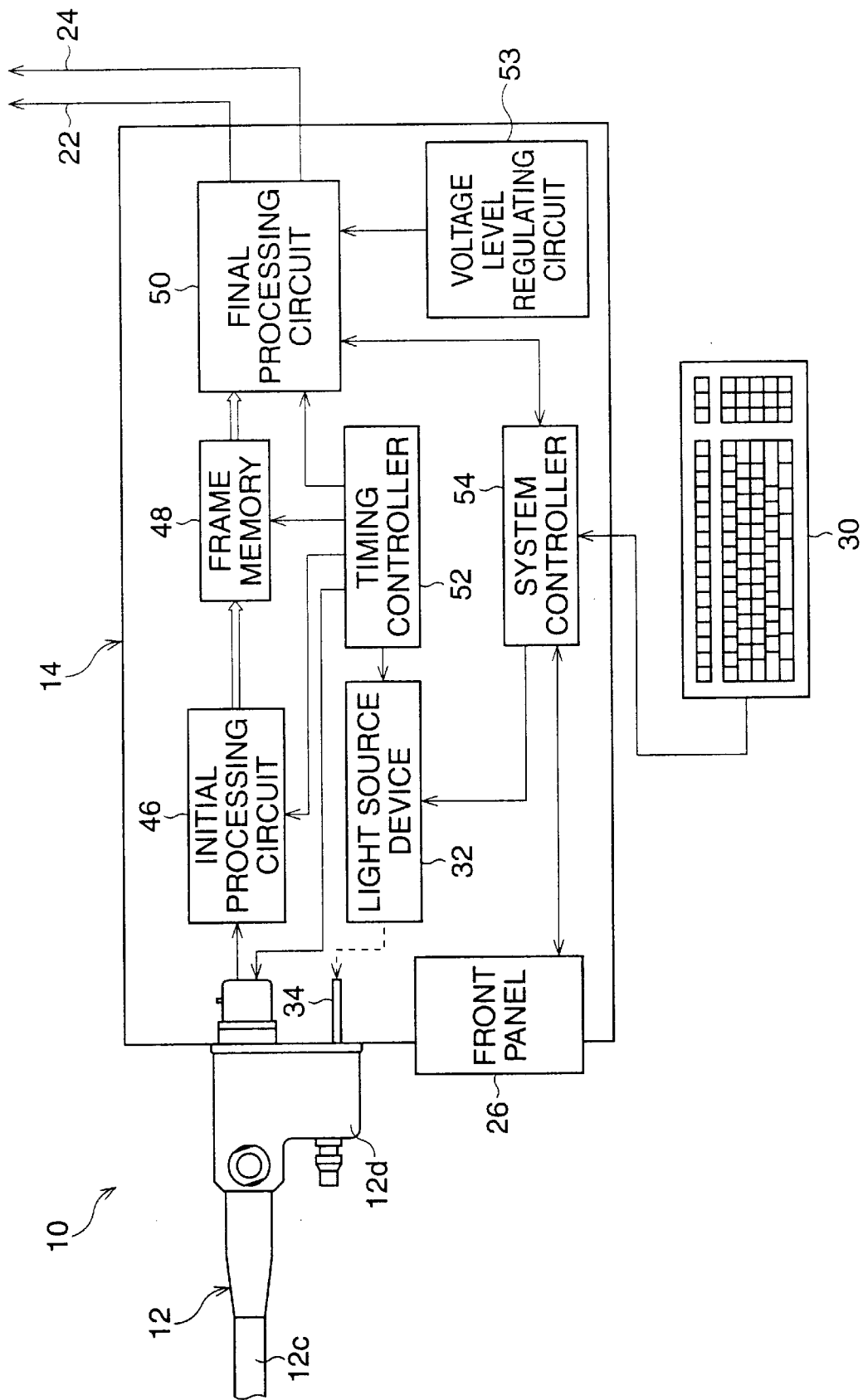
FIG. 2 is a schematic block diagram of an image-signal processing unit of the electronic endoscope system.

FIG. 2 schematically shows a block diagram of the image-signal processing unit 14.

The aforementioned light source device, provided in the image-signal processing unit 14, is indicated by reference 32. The optical light guide extending through the scope 12 has a rigid optical plug 34 joined to the proximal end thereof, such that the proximal end of the optical light guide is optically connected to the light source device 32 via the rigid optical plug 34. The rigid optical plug 34 is securely supported by the connector 12d, and is optically connected to the light source device 32 when the connector 12d is inserted in a socket (not shown), provided on the front wall of the housing of the image-signal processing unit 14. Note, in FIG. 2, the optical connection between the light source device 32 and the rigid optical plug 34 is represented by an arrow-headed broken line for convenience.

Figure 3:
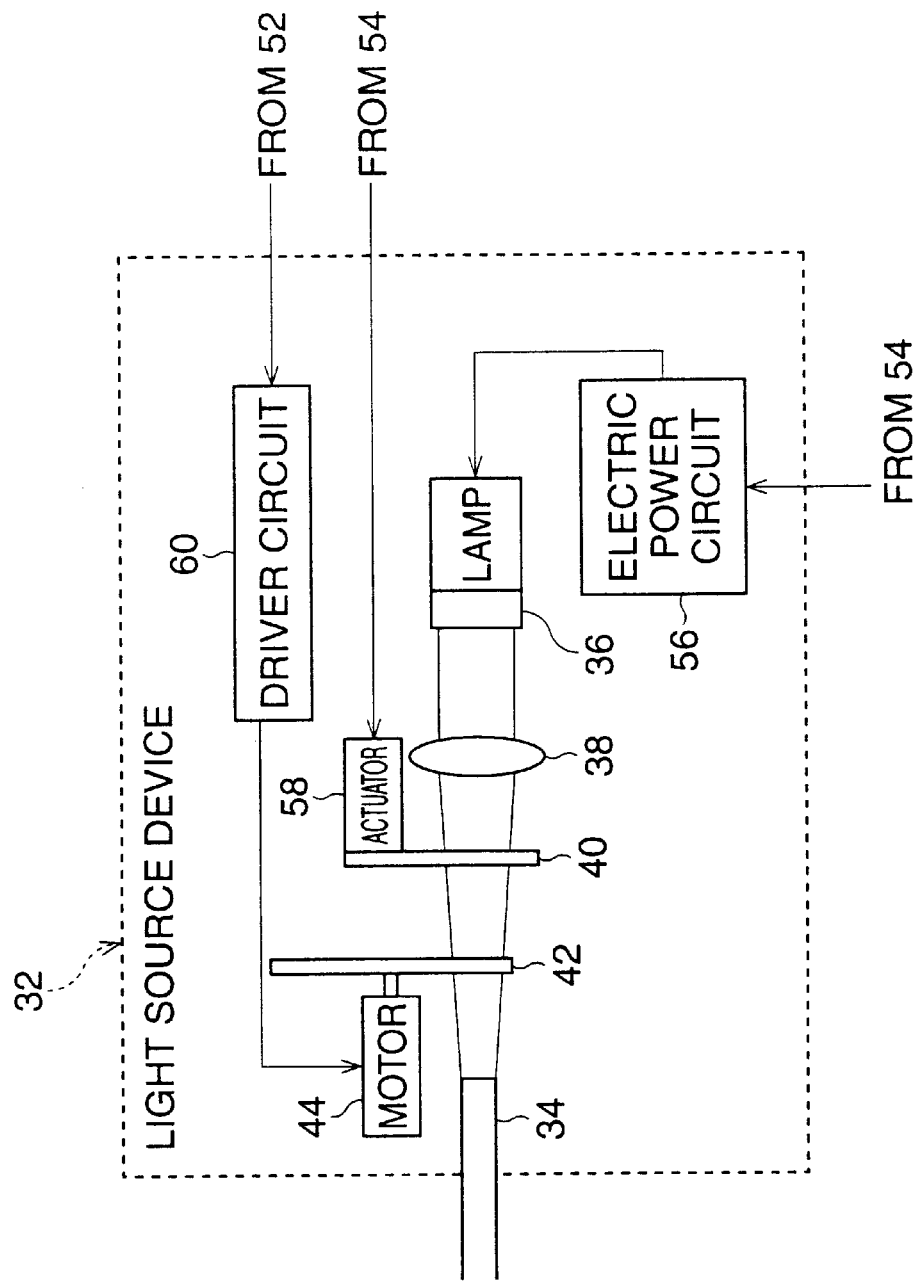
FIG. 3 is a schematic block diagram of a light source device provided in the image-signal processing unit.

As shown in FIG. 3, the light source device 32 includes a white lamp 36, such as a halogen lamp, a xenon lamp or the like, for emitting white light, a condenser lens 38 for converging the emitted white light onto the free end face of the rigid optical plug 34, and a diaphragm 40 for regulating the amount of white light directed from the white lamp 36 to the free end face of the rigid optical plug 34, i.e. the amount of illuminating-light radiating from the distal end of the optical light guide.

As mentioned above, since the RGB field sequential-type color imaging method is incorporated in the electronic endoscope system, a rotary color filter disk 42 is interposed between the diaphragm 38 and the free end face of the rigid optical plug 34. The rotary RGB color filter disk 42 has three sector-shaped color filters, i.e. red, green and blue filters, and these color filters are circumferentially and uniformly arranged such that three centers of the color filters are spaced from each other at regular angular-intervals of 120 degrees, with a sector area between two adjacent color filters serving as a light-shielding area.

The rotary RGB color filter disk 42 is rotated by a suitable electric motor 44, such as a servo-motor, a stepping motor or the like, at a given rotational frequency in accordance with a commonly used image-reproduction method, such as NTSC, PAL and so on, whereby the object to be captured by the CCD image sensor is sequentially illuminated by red light, green light and blue light. Namely, a red optical image, a green optical image and a blue optical image are sequentially and cyclically focused on the light-receiving surface of the CCD image sensor.

Note, in the NTSC system, the rotational frequency of the color filter disk 42 is 30 Hz, and, in the PAL system, the rotational frequency of the color filter disk 42 is 25 Hz.

Each of the red, green and blue optical images is sequentially converted into a frame of monochromatic (red, green, blue) analog image-pixel signals by the CCD image sensor, and the monochromatic (red, green, blue) analog image-pixel signals are read from the CCD image sensor over consecutive light-shielding time periods corresponding to the light-shielding areas between two adjacent color filters. The monochromatic analog image-pixel signals are then fed to the image-signal processor provided in the image-signal processing unit 14.

As shown in FIG. 2, the image-signal processor, provided in the image-signal processing unit 14, includes an initial processing circuit 46, a frame memory 48 and a final processing circuit 50, and is sequentially and systematically operated in accordance with various series of clock pulses output from a timing controller 52. Note, the reading of the monochromatic analog image-pixel signals from the CCD image sensor is performed by operating the aforesaid CCD driver in accordance with clock pulses output from the timing controller 52, which is operated under control of a system controller 54.

The monochromatic analog image-pixel signals, fed to the image-signal processor, are suitably processed in the initial processing circuit 46 under control of the timing controller 52. For example, the monochromatic analog image-pixel signals are subjected to white-balance correction, gamma-correction, profile-enhancing and so on. Then, the processed monochromatic analog image-pixel signals are converted into monochromatic digital image-pixel signals by an analog-to-digital converter provided in the initial processing circuit 46.

The monochromatic digital image-pixel signals are temporarily stored in the frame memory 48. In the frame memory 48, three memory sections are defined for the storage of red, green and blue digital image-pixel signals, respectively. In short, the monochromatic digital image-pixel signals are stored in respective memory sections, defined in the frame memory 48, that correspond to each image pixel color.

While the monochromatic digital image-pixel signals are successively stored in the frame memory 48, the respective red, green and blue digital image-pixel signals are simultaneously read from the three frame memory sections of the frame memory 48 in accordance with a series of timing clock pulses output from the timing controller 52, and are output to the final processing circuit 50 as red, green and blue digital video signal components, respectively. The timing controller 52 also produces a compound-synchronizing-signal component, and outputs it to the final processing circuit 50. Thus, the component-type video signal is produced and processed in the final processing circuit 50. Thereafter, the component-type video signal is output as an analog component-type video signal from the final processing circuit 50 to the TV monitor 16, as stated in detail hereinafter.

Note, in FIG. 2, the aforesaid voltage-level-regulating circuit, formed on the circuit board 28, is indicated by reference 53, and is connected to the final processing circuit 50 to regulate the peak-to-peak level of the compound-synchronizing-signal component.

The system controller 54 is constituted as a microcomputer, used to control the electronic endoscope system as a whole, which comprises a central processing unit (CPU), a read-only memory (ROM) for storing programs and constants, a random-access memory (RAM) for storing temporary data, and an input/output interface circuit (I/O).

For example, in FIG. 3, an electric power circuit 56, for electrically energizing the white light 36, is operated under control of the system controller 54. Also, an actuator 58, for driving the diaphragm 40, is operated under control of the system controller 54 so that the brightness of the display of the TV monitor 16 is constant. Further, a driver circuit 60, for driving the motor 44 of the rotary RGB color filter disk 43, is driven in accordance with a series of drive clock pulses output from the timing controller 52.

Figure 4:
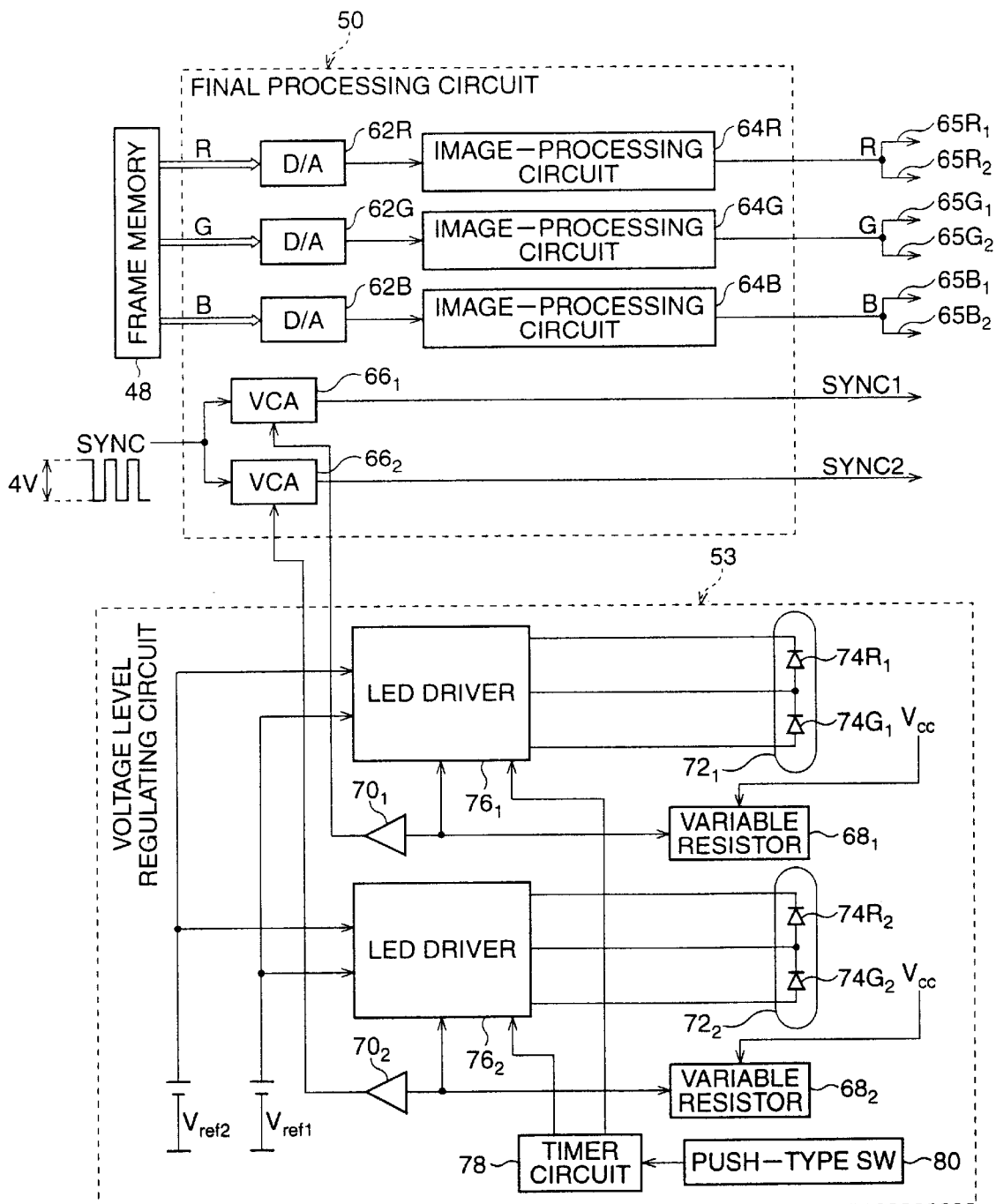
FIG. 4 is a schematic block diagram of a voltage-level-regulating circuit associated with a final processing circuit of an image-signal processor provided in the image-signal processing unit.

FIG. 4 shows a block diagram of the final processing circuit 50. As is apparent from this drawing, the final processing circuit 50 includes three digital-to-analog (D/A) converters 62R, 62G and 62B, and three image-processing circuits 64R, 64G and 64B. The respective digital red, green and blue video signal components (R, G and B), output from the frame memory 48, are converted into analog red, green and blue video signal components by the D/A converters 62R, 62G and 62B, and then the respective analog red, green and blue video signal components are suitably processed in the image-processing circuits 64R, 64G and 64B. For example, the red, green and blue video signal components (R, G and B) are subjected to a color-balance processing, a noise-filtering processing and so on, and then are output from the image-signal processing unit 14.

As shown in FIG. 4, each output-signal line extending from the image-processing circuits 64R, 64G and 64B terminates at a fork having two output terminals ($65R_1$, $65R_2$; $65G_1$, $65G_2$; $65B_1$, $65B_2$), so that two sets of red, green and blue video signal components (R, G and B) are output from the image-processing circuits 64R, 64G and 64B.

The final processing circuit 50 also includes a first voltage-controlled amplifier (VCA) $66_1$ and a second voltage-controlled amplifier (VCA) $66_2$, and the compoundsynchronizing-signal component (SYNC), output from the timing controller 52, is input to the first and second VCA's $66_1$ and $66_2$. In the timing controller 52, the compound synchronizing-signal component (SYNC) is produced as a voltage signal exhibiting a peak-to-peak level of 4 volts, and each of the first and second VCA's $66_1$ and $66_2$ is provided to discretely regulate the peak-to-peak level of the compound-synchronizing-signal component. In FIG. 4, the compound-synchronizing-signal component, output from the first VCA $66_1$, is indicated by reference SYNC1, and the compound-synchronizing-signal component, output from the second VCA $66_2$, is indicated by reference SYNC2.

In short, in this embodiment, the final processing circuit 50 outputs two sets of component-type color video signals: a first component-type color video signal composed of the primary-color video signal components (R, G and B) and the synchronizing-signal component (SYNC1); and a second component-type color video signal composed of the primary-color video signal components (R, G and B) and the synchronizing-signal component (SYNC2).

As is well known, the amplification factor of each VCA ($66_1$, $66_2$) is altered in accordance with a level of voltage applied. Thus, it is possible to regulate the peak-to-peak level (4 volts) of each synchronizing-signal component (SYNC1, SYNC2) by adjusting the voltage applied to the corresponding VCA ($66_1$, $66_2$). The adjustment of the voltage applied to each VCA ($66_1$, $66_2$) is performed by the voltage-level-regulating circuit 53 formed on the circuit board 28. In this embodiment, the regulation of the peak-to-peak level of each synchronizing-signal component is continuously performed within a range of 0 to 4 volts, as stated in detail hereinafter.

As shown in FIG. 4, the voltage-level-regulating circuit 53 includes a first variable resistor $68_1$ for regulating the amplification factor of the first VCA $66_1$, and a second variable resistor $68_2$ for regulating the amplification factor of the second VCA $66_2$, and the respective first and second variable resistors $68_1$ and $68_2$ are connected to the first and second VCA's $66_1$ and $66_2$ via first and second buffers $70_1$ and $70_2$. As is apparent from FIG. 4, a predetermined voltage $V_{cc}$ is applied to each of the first and second resistors $68_1$ and $68_2$. In this embodiment, the voltage $V_{cc}$ is 4 volts, and each of the first and second buffers $70_1$ and $70_2$ exhibits an amplification factor of "1". A voltage, applied to each VCA ($66_1$, $66_2$), is adjusted within a range of 0 to 4 volts by manually operating the corresponding variable resistor ($68_1$, $66_2$).

Figure 5:
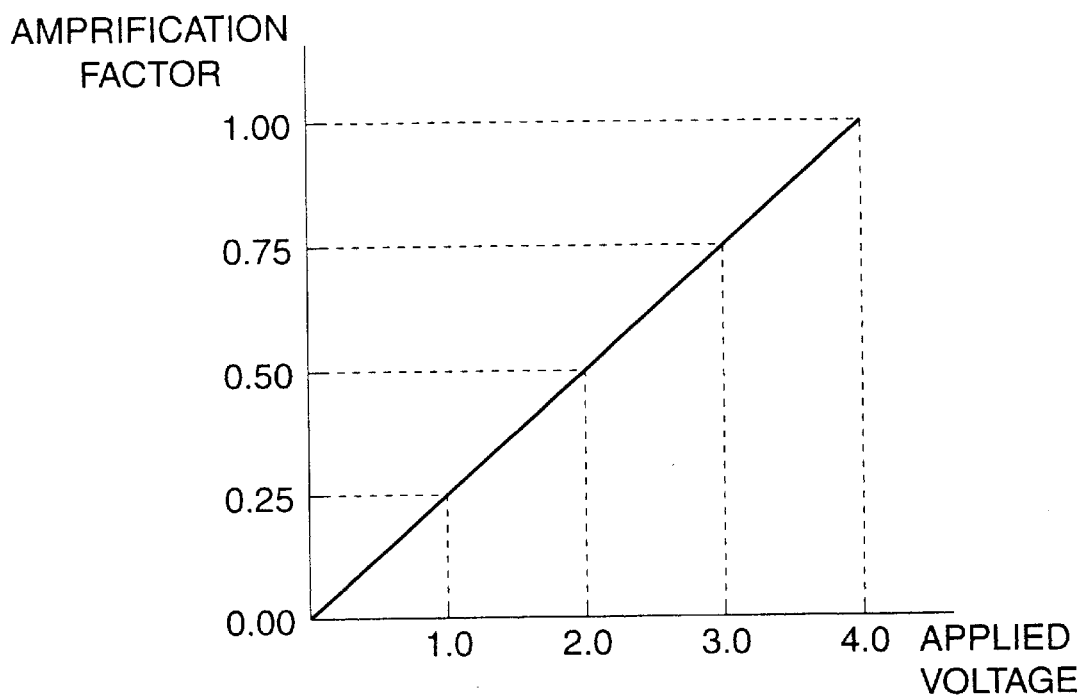
FIG. 5 is a graph showing a relationship between an amplification factor of a voltage-controlled amplifier, provided in the final processing circuit, and voltage applied to the voltage-controlled amplifier.

With reference to a graph of FIG. 5, a relationship is shown between the amplification factor of each VCA ($66_1$, $66_2$) and the voltage applied thereto.

For example, when the first variable resistor $68_1$ is adjusted such that 4 volts is applied to the first VCA $66_1$, the amplification factor in the first VCA $66_1$ is 1.00, and thus the first synchronizing-signal component (SYNC1), output from the first VCA $66_1$, exhibits the peak-to-peak level of 4 volts as the amplification factor is 1.00. When adjustments of the first variable resistor $68_1$ are performed such that respective 3.0, 2.0 and 1.0 volts are applied to the first VCA $66_1$, respective settings of 0.75, 0.50 and 0.25 are given to the first VCA $66_1$, so that the first synchronizing-signal component (SYNC1), output from the first VCA $66_1$, exhibits the respective peak-to-peak levels of 3, 2 and 1 volts. Of course, regulation of the peak-to-peak level of the second synchronizing-signal component (SYNC2) is performed in substantially the same manner as mentioned above.

As shown in FIG. 4, the first resistor $68_1$ is associated with a first indicator lamp $72_1$ to indicate a level of adjusted voltage applied to the first VCA $66_1$, i.e. the regulated peak-to-peak level of the first synchronizing-signal component SYNC1. The first indicator lamp $72_1$ comprises a light bulb containing two light-emitting diodes (LED) $74G_1$ and $74R_1$, and lighting of the LED's $74G_1$ and $74R_1$ is controlled by a first LED driver $76_1$.

Similarly, the second resistor $68_2$ is associated with a second indicator lamp $72_2$ to indicate a level of adjusted voltage applied to the second VCA $66_2$, i.e. the regulated peak-to-peak level of the second synchronizing-signal component SYNC2. The second indicator lamp $72_2$ comprises a light bulb containing two light-emitting diodes (LED) $74G_2$ and $74R_2$, and lighting of the LED's $74G_2$ and $74R_2$ is controlled by a second LED driver $76_2$.

Note, when each of the LED's $74G_1$ and $74G_2$ is powered ON, it emits green light, and, when each of the LED's $74R_1$ and $74R_2$ is powered ON, it emits red light.

As is apparent from FIG. 4, the voltage, output from the first resistor $68_1$, is applied to not only the first VCA $66_1$ but also the first LED driver $76_1$, and first and second reference voltages $V_{ref1}$ and $V_{ref2}$ are further applied to the first LED driver $76_1$. In the first LED driver $76_1$, the output voltage of the first resistor $68_1$ is compared with the reference voltages $V_{ref1}$ and $V_{ref2}$, and the lighting control of the LED's $74G_1$ and $74R_1$ is performed in accordance with the comparison of the output voltage with the first and second reference voltages $V_{ref1}$ and $V_{ref2}$.

Figure 6:
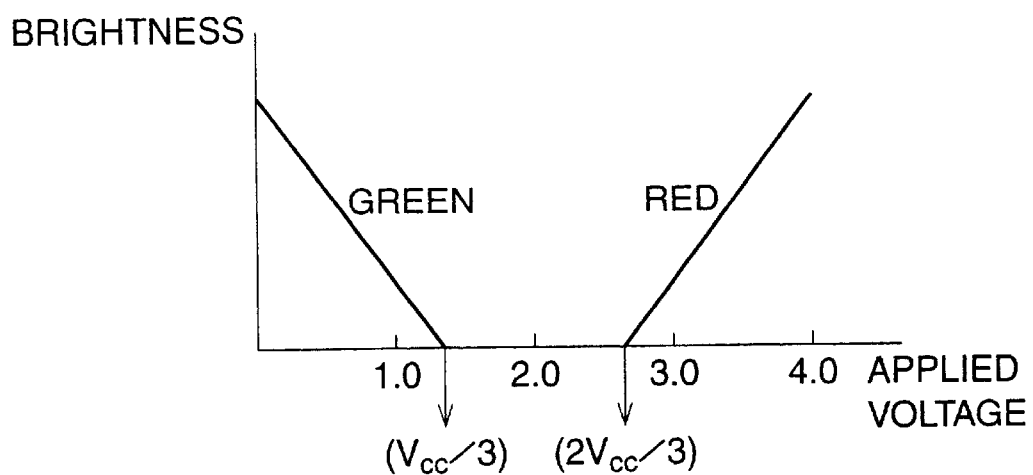
FIG. 6 is a graph representing lighting control of an indicator lamp having a green LED and a red LED for indicating a level of adjusted voltage applied to the voltage-controlled amplifier.

With reference to FIG. 6, the lighting control of the LED's $74G_1$ and $74R_1$ is graphically represented by way of example. In this example, the first reference voltage $V_{ref1}$ is set as $V_{cc}/3$, and the second reference voltage $V_{ref2}$ is set as $2 V_{cc}/3$. Namely, the output voltage range (from 0 to 4 volts) of the first resistor $68_1$ is divided by the first and second reference voltages $V_{ref1}$ and $V_{ref2}$ into three regular sections.

In particular, for example, when the output voltage of the first resistor $68_1$ is lower than the first reference voltage $V_{ref1}$ ($V_{cc}/3$), only the green LED $74G_1$ is lit. When the output voltage of the first resistor $68_1$ is at the zero level, the brightness of the lit green LED $74G_1$ is at the maximum level. As the output voltage of the first resistor $68_1$ is increased from the zero level toward the first reference voltage $V_{ref1}$, the brightness of the lit green LED $74G_1$ is gradually reduced toward the minimum level.

When the output voltage of the first resistor $68_1$ reaches the first reference voltage $V_{ref1}$, the green LED $74G_1$ is turned OFF. When the output voltage of the first resistor $68_1$ is in the range between the first and second reference voltages $V_{ref1}$ and $V_{ref2}$, both the green and red LED's $74G_1$ and $74R_1$ are turned OFF.

As soon as the output voltage of the first resistor $68_1$ exceeds the second reference voltage $V_{ref2}$, only the red LED $74R_1$ is lit at the minimum level. As the output voltage of the first resistor $68_1$ is increased from the second reference voltage $V_{ref2}$ toward the maximum voltage (4 volts), the brightness of the lit red LED $74R_1$ is gradually increased toward the maximum level.

Similarly, the voltage, output from the second resistor $68_2$, is applied to not only the second VCA $66_1$ but also the second LED driver $76_2$, and the first and second reference voltages $V_{ref1}$ and $V_{ref2}$ are further applied to the second LED driver $76_2$. In the second LED driver $76_2$, the output voltage of the second resistor $68_2$ is compared with the reference voltages $V_{ref1}$ and $V_{ref2}$, and the lighting control of the LED's $74G_2$ and $74R_2$ is performed in substantially the same manner as mentioned above.

Of course, the above-mentioned adjustments are described in a manual guidance text for an electronic endoscope system or the adjustments are previously announced to maintenance persons. Thus, while watching each of the first and second indicator lamps $72_1$ and $72_2$, a maintenance person can suitably and properly regulate the peak-to-peak level of the corresponding synchronizing-signal component (SYNC1, SYNC2).

For example, in the manual guidance text, the following messages may be described:

(1) "FOR X-TYPE MONITOR OF A-COMPANY, ADJUST RESISTOR SUCH THAT LAMP IS LIT AT DARK GREEN BRIGHTNESS";

(2) "FOR Y-TYPE MONITOR OF B-COMPANY, ADJUST RESISTOR SUCH THAT BOTH LAMPS ARE TURNED OFF, BUT BIASED TOWARD the GREEN-LIGHT-EMITTING SIDE"; and (3) "FOR Z-TYPE MONITOR OF C-COMPANY, ADJUST RESISTOR SUCH THAT THE LAMP IS A CLEAR RED BRIGHTNESS"

As shown in FIG. 4, the first and second LED drivers $76_1$ and $76_2$ are associated with a timer circuit 78 having a push-type switch 80. When the push-type switch 80 is turned ON, an ON-signal is output to the timer circuit 78, whereby the first and second LED drivers $76_1$ and $76_2$ are electrically energized for a given time, for example, 5 minutes, previously set by the timer circuit 80. Namely, in this embodiment, the first and second indicator lamps $72_1$ and $72_2$ are lit for only 5 minutes which is considered enough time to regulate the peak-to-peak level of each synchronizing-signal component (SYNC1, SYNC2).

Figure 7:
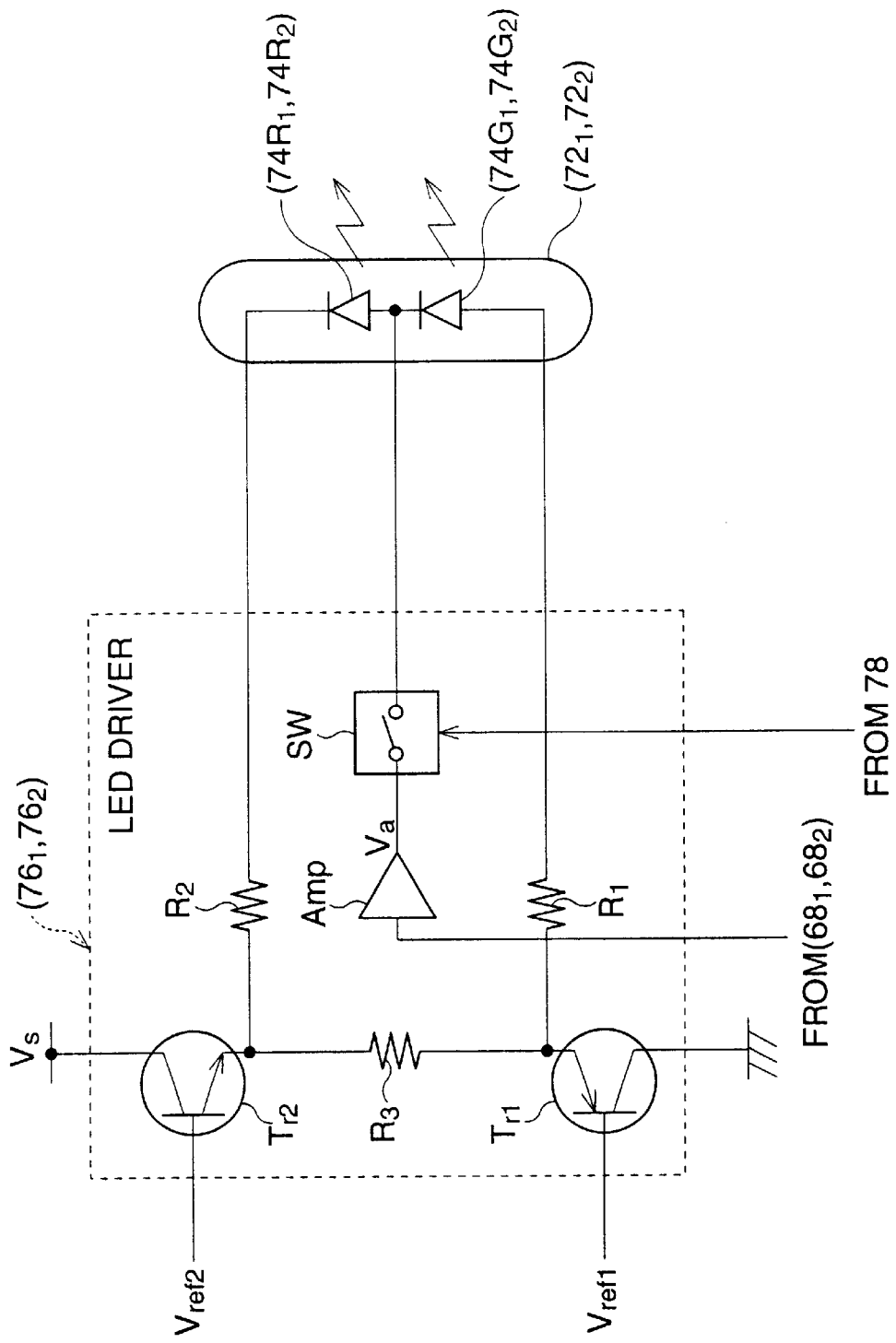
FIG. 7 is a wiring diagram of an LED driver for the lighting control of the green and red LED's of the indicator lamp.

With reference to FIG. 7, a wiring diagram of the first and second LED drivers $76_1$ and $76_2$ is shown, by way of example, to achieve the lighting control of each indicator lamp ($72_1$, $72_2$) as shown in the graph of FIG. 6. Each of the first and second LED drivers ($76_1$, $76_2$) is formed from a PNP-type transistor $Tr_1$, a NPN-type transistor $Tr_2$, an amplifier Amp, an ON/OFF switch SW, and three resistors $R_1$, $R_2$ and $R_3$.

The respective first and second reference voltages $V_{ref1}$ and $V_{ref2}$ are applied to the base of the transistors $Tr_1$ and $Tr_2$. The collector of the first transistor $Tr_1$ is grounded, and the emitter thereof is connected to the anode of the green LED ($74G_1$, $74G_2$) of the indicator lamp ($72_1$, $72_2$) via a resistor $R_1$ which has a suitable resistance value. A suitable voltage Vs (e.g. 4 volts) is applied to the collector of the transistor $Tr_2$, and the emitter thereof is connected to the cathode of the red LED ($74R_1$, $74R_2$) of the indicator lamp ($72_1$, $72_2$) via a resistor $R_2$ which has a suitable resistance value. The emitters of the transistors $Tr_1$ and $Tr_2$ are connected to each other via a resistor $R_3$ which has a suitable resistance value.

Also, as shown in FIG. 7, an output terminal of the amplifier Amp is connected to both the anode of the red LED ($74R_1$, $74R_2$) and the cathode of the green LED ($74G_1$, $74G_2$) via the ON/OFF switch SW. The output voltage of the variable resistor ($68_1$, $68_2$) is input to an input terminal of the amplifier Amp. The ON/OFF switch SW is controlled by the timer circuit 78 such that an ON-state of the ON/OFF switch SW is maintained for 5 minutes from when the push-type switch 80 is turned ON. The amplifier Amp exhibits an amplification factor of "1", and thus the output voltage of the variable resistor ($68_1$, $68_2$) is applied as it stands to both the anode of the red LED ($74R_1$, $74R_2$) and the cathode of the green LED ($74G_1$, $74G_2$) while the ON/OFF switch SW is in the ON-state. Note, in FIG. 7, the voltage, output from the amplifier Amp, is represented by reference $V_a$.

With the above-mentioned arrangement of the wiring diagram of the LED driver ($76_1$, $76_2$), if the output voltage of the variable resistor ($68_1$, $68_2$) is smaller than the first reference voltage $V_{ref1}$ ($V_a < V_{ref1}$), an electric current flows only through the green LED ($74G_1$, $74G_2$), thereby lighting only the green LED ($74G_1$, $74G_2$). As the output voltage ($V_a$) of the variable resistor ($68_1$, $68_2$) is increased toward the first reference voltage $V_{ref1}$, the amount of electric current flowing through the green LED ($74G_1$, $74G_2$) gradually reduces. Thus, the brightness of the lit green LED ($74G_1$, $74G_2$) is gradually reduced toward the minimum level, as shown in the graph of FIG. 6.

When the output voltage ($V_a$) of the resistor ($68_1$, $68_2$) reaches the first reference voltage $V_{ref1}$, the electric current cannot flow any longer through the green LED ($74G_1$, $74G_2$), thereby turning the green LED ($74G_1$, $74G_2$) OFF. While the output voltage ($V_a$) of the resistor ($68_1$, $68_2$) is in the range between the first and second reference voltages $V_{ref1}$ and $V_{ref2}$, an electric current cannot flow through both the green ($74G_1$, $74G_2$) and the red LED ($74R_1$, $74R_2$), i.e. the OFF-states of both the green ($74G_1$, $74G_2$) and the red LED ($74R_1$, $74R_2$) are maintained, as shown in the graph of FIG. 6.

When the output voltage ($V_a$) of the resistor ($68_1$, $68_2$) exceeds the second reference voltage $V_{ref2}$, an electric current flows only through the red LED ($74R_1$, $74R_2$), thereby lighting only the red LED ($74R_1$, $74R_2$). As the output voltage ($V_a$) of the variable resistor ($68_1$, $68_2$) increases toward the second reference voltage $V_{ref2}$, the amount of electric current flowing through the red LED ($74R_1$, $74R_2$) gradually increases. Thus, the brightness of the lit red LED ($74R_1$, $74R_2$) is gradually increased toward the maximum level, as shown in the graph of FIG. 6.

Figure 8:
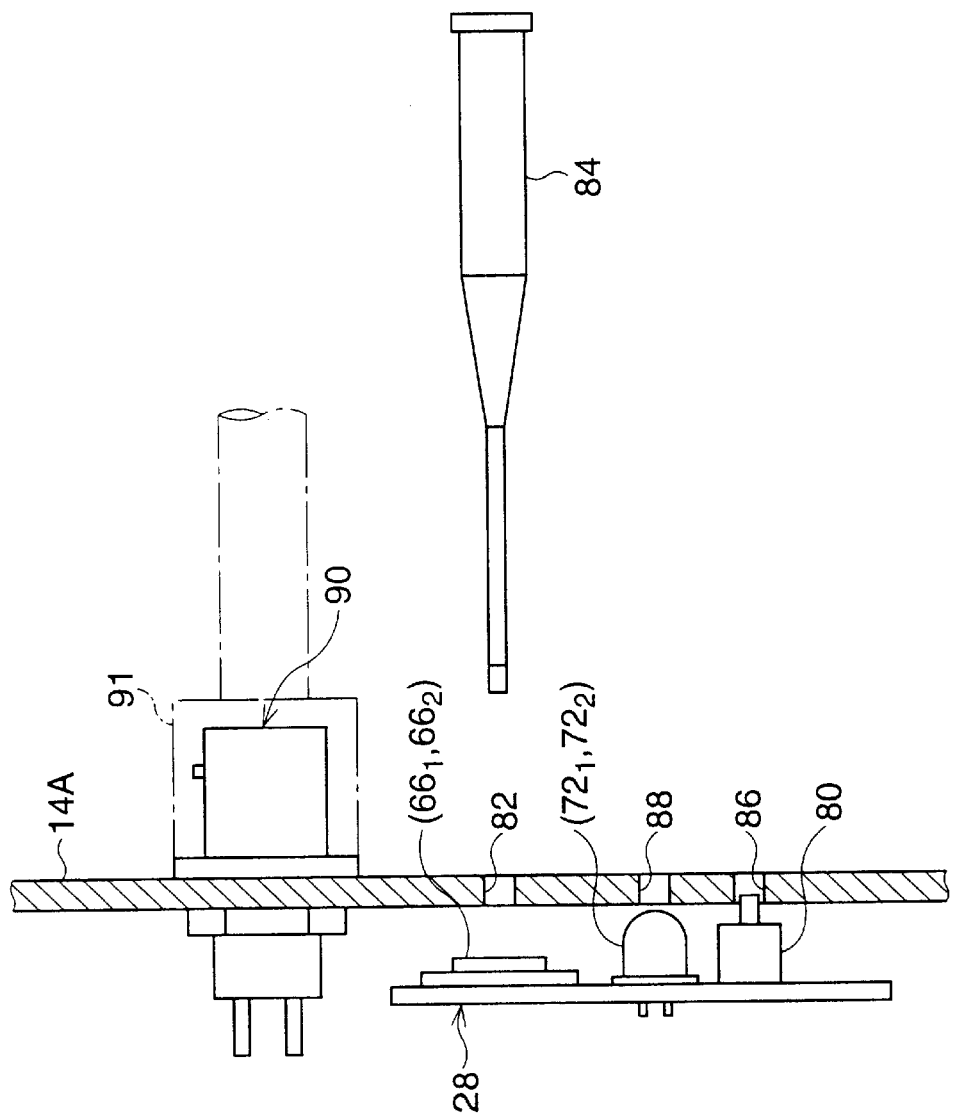
FIG. 8 is a cross-sectional view partially showing a rear wall of a housing of the image-signal processing unit.

FIG. 8 partially and cross-sectionally shows a rear wall, indicated by reference 14A, of the housing of the image-signal processing unit 14. As shown in this drawing, the circuit board 28, on which the voltage-level-regulating circuit 53 is formed, is placed in the vicinity of the rear wall 14A of the unit housing. Note, of course, although the circuit board 28 is provided with the first and second variable resistors $66_1$ and $66_2$, the first and second indicator lamps $72_1$ and $72_2$ and the two push-type switches 80, only one in each of these sets is representatively shown in FIG. 8.

The variable resistor ($66_1$, $66_2$) is arranged such that an operating section thereof is aligned with a through hole 82 formed in the rear wall 14A, and thus the operating section can be manually operated using a suitable tool such as a screw driver 84. Also, each of the push-type switches 80 is arranged such that a push button thereof is aligned with a through hole 86 formed in the rear wall 14A, and thus the push button can be manually operated by the screw driver 84. Further, the indicator lamp ($72_1$, $72_2$) is arranged to be aligned with a through hole 88 formed in the rear wall 14A, such that an light emission of the indicator lamp ($72_1$, $72_2$) is visible by a maintenance person.

In FIG. 8, reference 90 indicates an output terminal connector for the synchronizing-signal component (SYNC1, SYNC2). For example, the output terminal connector 90 forms a half of a BNC-type connector, and the other half 91 of the BNC-type connector is attached to one end of a co-axial cable for the synchronizing-signal component (SYNC1, SYNC2), as shown by phantom lines in FIG. 8.

Although the through hole 82 is adjacent to the output terminal connector 90, the screw driver 84 is operable without interfering with the co-axial cable extending from the output terminal connector 90, as is apparent from FIG. 8. Thus, while watching the TV monitor 16, a maintenance person may perform an adjustment of the variable resistor ($66_1$, $66_2$). Namely, when it is impossible or difficult to observe an light emission of the indicator lamp ($72_1$, $72_2$), the maintenance person can try the adjustment of the variable resistor ($66_1$, $66_2$) by watching the TV monitor 16.

With the arrangement as shown in FIG. 8, it is possible to prevent the variable resistor ($66_1$, $66_2$) from being accidentally operated during movement of the image-signal processing unit 14 and/or cleaning thereof. Of course, whenever the variable resistor ($66_1$, $66_2$) is accidentally operated, it is necessary to readjust the peak-to-peak level of the synchronizing-signal component (SYNC1, SYNC2).

Figure 9:
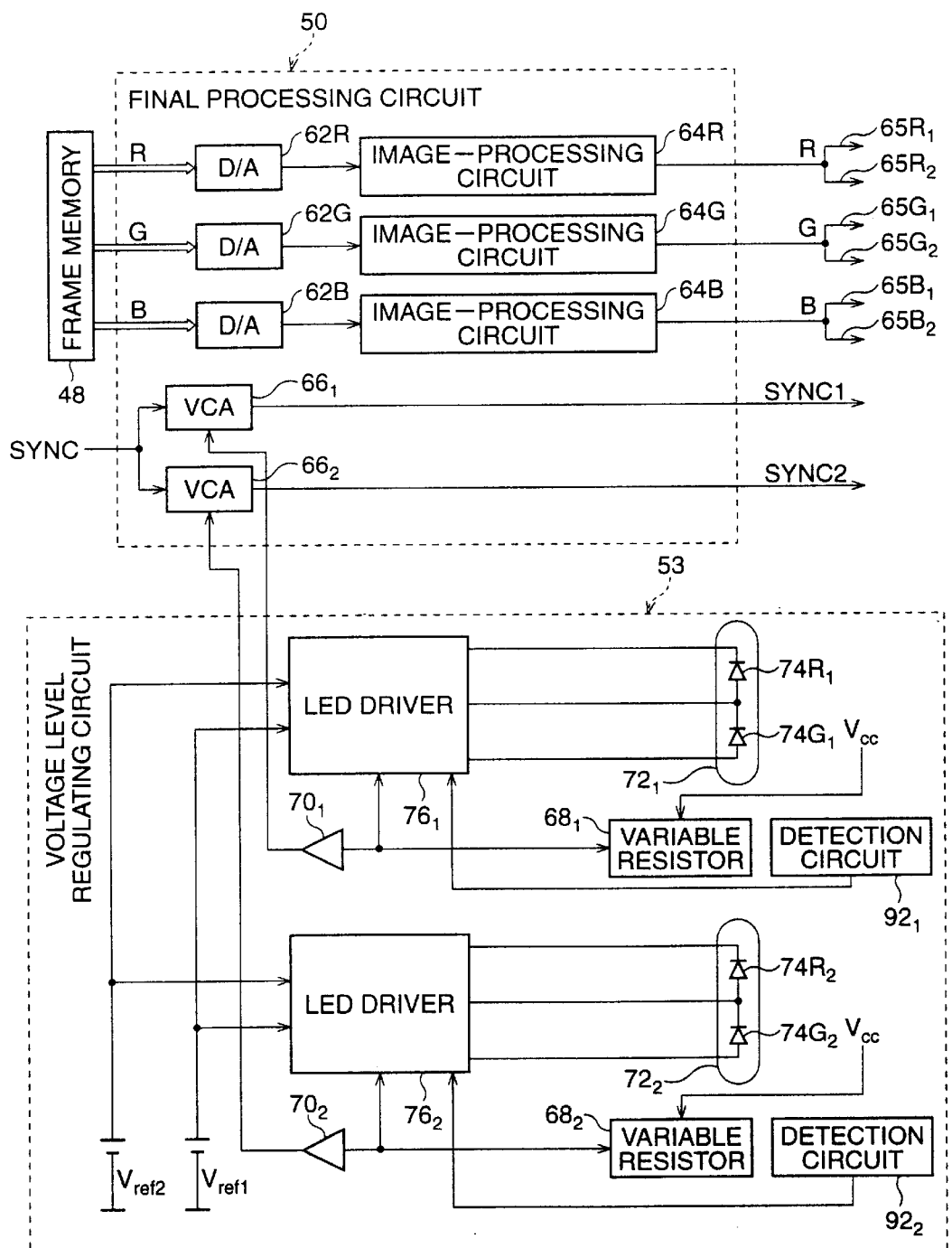
FIG. 9 is a schematic block diagram, similar to FIG. 4, showing a modification of the voltage-level-regulating circuit.
Figure 10:
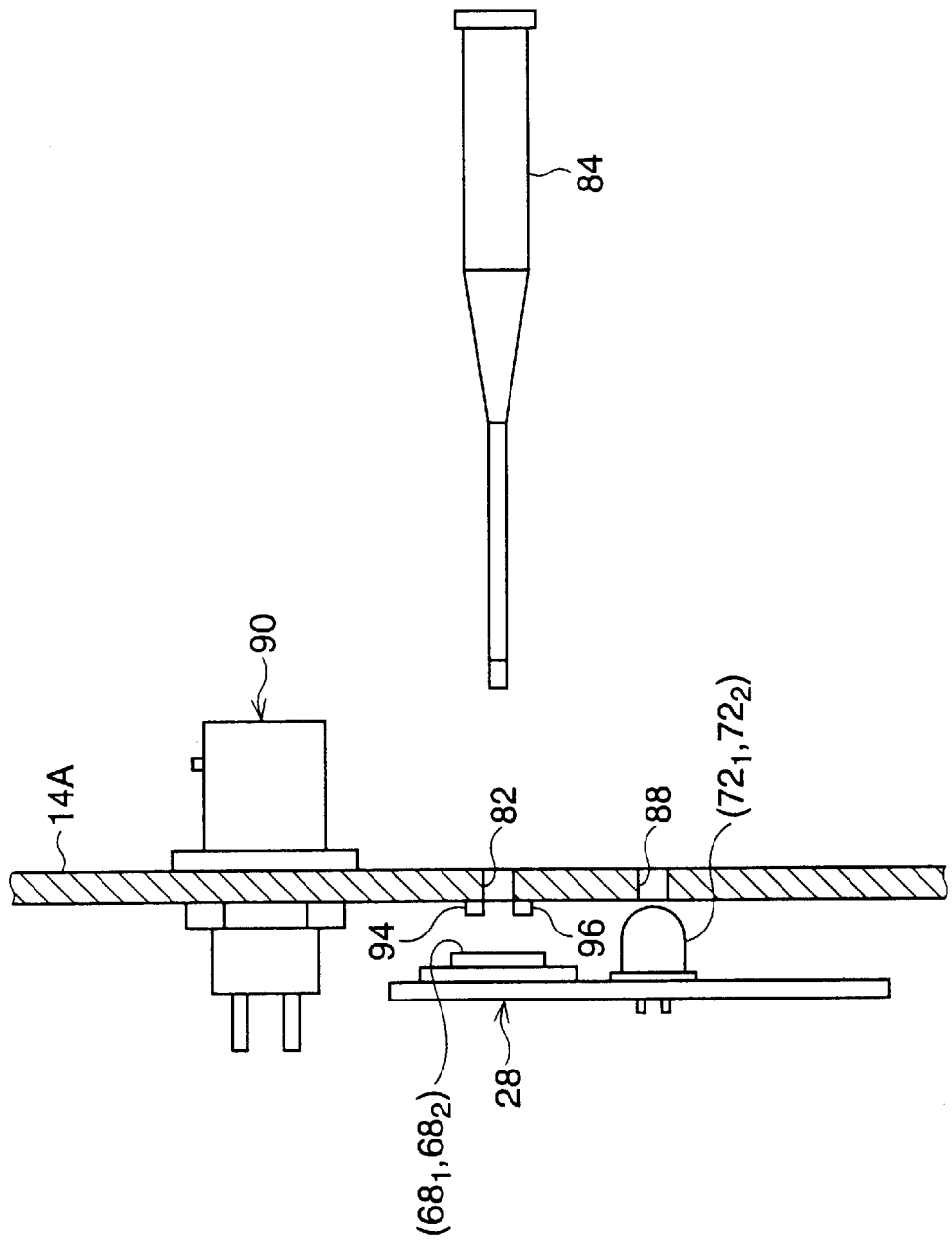
FIG. 10 is a cross-sectional view, similar to FIG. 8, according to the modification of the voltage-level-regulating circuit shown in FIG. 9.

FIGS. 9 and 10 show a modification of the voltage-level-regulating circuit 53 shown in FIG. 4. In this modification, the timer circuit 78 and the push-type switch 80 are omitted as shown in FIG. 9, and first and second detection circuits $92_1$ and $92_2$ are substitutively associated with the first and second variable resistors $68_1$ and $68_2$. The first detection circuit $92_1$ is connected to the ON/OFF switch SW (FIG. 7) of the first LED driver $76_1$, and the second detection circuit $92_2$ is connected to the ON/OFF switch SW (FIG. 7) of the second LED driver $76_2$. As shown in FIG. 10, each of the first and second detection circuits $92_1$ and $92_2$ includes a light-emitting element 94, such as an light-emitting diode, and a light-receiving element 96, such as a photodiode, which are securely attached to an inner wall face of the rear wall 14A in the vicinity of the through hole 82 such that the elements 94 and 96 are circumferentially and diametrically arranged with respect to the through hole 82.

The light-emitting element 94 emits light, which is received by the light-receiving element 96. In this case, the detection circuit ($92_1$, $92_2$) outputs an OFF-signal to the ON/OFF switch SW of the LED driver circuit ($76_1$, $76_2$), and thus the ON/OFF switch SW concerned is in the OFF-state. When the screw driver 84 is inserted into the through hole 82 to adjust the variable resistor ($68_1$, $68_2$), i.e. when the light, emitted from the light-emitting element 94, is blocked off by the inserted screw driver 84 and thus not received by the light-receiving element 76, the detection circuit ($92_1$, $92_2$) outputs an ON-signal to the ON/OFF switch SW of the LED driver circuit ($76_1$, $76_2$), and thus the ON/OFF switch SW concerned is turned ON, whereby the LED driver circuit ($76_1$, $76_2$) can electrically power ON the indicator lamp ($72_1$, $72_2$). Namely, while adjusting the variable resistor ($68_1$, $68_2$) with the screw driver 84, the green and red LED's ($74G_1$ and $74R_1$; $74G_2$ and $74R_2$) of the indicator lamp ($72_1$, $72_2$) are lit as explained with reference to the graph of FIG. 6.

In the aforementioned embodiments, although the lighting control of the green and red LED's ($74G_1$ and $74R_1$; $74G_2$ and $74R_2$) is performed in accordance with the comparison of the output voltage of the variable resistor ($68_1$, $68_2$) with the two reference voltages $V_{ref1}$ and $V_{ref2}$, a single reference voltage or more than two reference voltages may be utilized for the lighting control of the green and red LED's ($74G_1$ and $74R_1$; $74G_2$ and $74R_2$).

For example, it is possible to control the lighting of the green and red LED's ($74G_1$ and $74R_1$; $74G_2$ and $74R_2$) by utilizing a single reference voltage, as shown in a graph of FIG. 11. Note, in this graph, the single reference voltage is set as $V_{cc}/2$, and thus the output voltage range (from 0 to 4 volts) of the resistor ($68_1$, $68_2$) is divided by the reference voltage ($V_{cc}/2$) into two regular sections.

Figure 11:
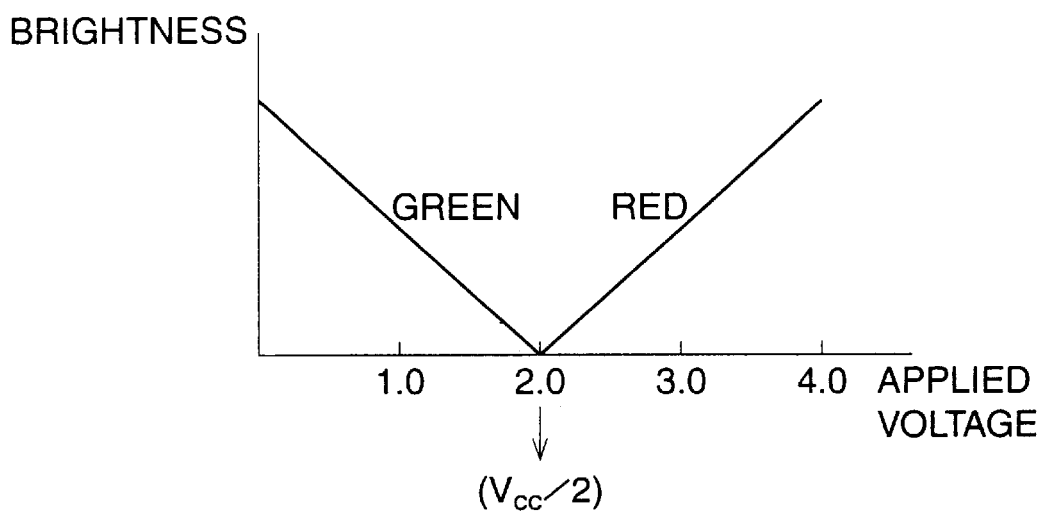
FIG. 11 is another graph representing the lighting control of an indicator lamp having a green LED and a red LED for indicating a level of adjusted voltage applied to the voltage-controlled amplifier.

In particular, for example, when the output voltage of the resistor ($68_1$, $68_2$) is lower than the reference voltage ($V_{cc}/2$), only the green LED ($74G_1$, $74G_2$) is lit. As shown in the graph of FIG. 11, when the output voltage of the resistor ($68_1$, $68_2$) is at the zero level, the brightness of the green LED ($74G_1$, $74G_2$) is at the maximum level. As the output voltage of the resistor ($68_1$, $68_2$) is increased from the zero level toward the reference voltage ($V_{cc}/2$), the brightness of the green LED ($74G_1$, $74G_2$) is gradually reduced toward the minimum level.

When the output voltage of the resistor ($68_1$, $68_2$) reaches the reference voltage ($V_{cc}/2$), the green LED ($74G_1$, $74G_2$) is turned OFF. As soon as the output voltage of the resistor ($68_1$, $68_2$) exceeds the reference voltage ($V_{cc}/2$), only the red LED ($74R_1$, $74R_2$) is lit. As the output voltage of the resistor ($68_1$, $68_2$) is increased from the reference voltage ($V_{cc}/2$) toward the maximum voltage (4 volts), the brightness of the red LED ($74R_1$, $74R_2$) is gradually increased toward the maximum level.

Thus, while watching the indicator lamp ($72_1$, $72_2$), the maintenance person can suitably and properly regulate the peak-to-peak level of the synchronizing-signal component (SYNC1, SYNC2). Note, of course, it can be easily realized by those skilled in the art, that the first and second LED driver $76_1$ and $76_2$ are designed and constituted such that the lighting control of the green and red LED's ($74G_1$ and $74R_1$; $74G_2$ and $74R_2$) is performed as shown in the graph of FIG. 11.

Further, it is possible to perform the lighting control of the green and red LED's ($74G_1$ and $74R_1$; $74G_2$ and $74R_2$) by utilizing three reference voltages, as shown in a graph of FIG. 12. Note, in this graph, the three reference voltages: first, second and third reference voltages are set as $V_{cc}/4$, $V_{cc}/2$ and $3V_{cc}/4$, and thus the output voltage range (from 0 to 4 volts) of the resistor ($68_1$, $68_2$) is divided by the reference voltages ($V_{cc}/4$, $V_{cc}/2$ and $3V_{cc}/4$) into four regular sections.

In particular, when the output voltage of the resistor ($68_1$, $68_2$) is lower than the second reference voltage ($V_{cc}/2$), only the green LED ($74G_1$, $74G_2$) is lit. Also, when the output voltage of the resistor ($68_1$, $68_2$) is higher than the second reference voltage ($V_{cc}/2$), only the red LED ($74R_1$, $74R_2$) is lit.

Figure 12:
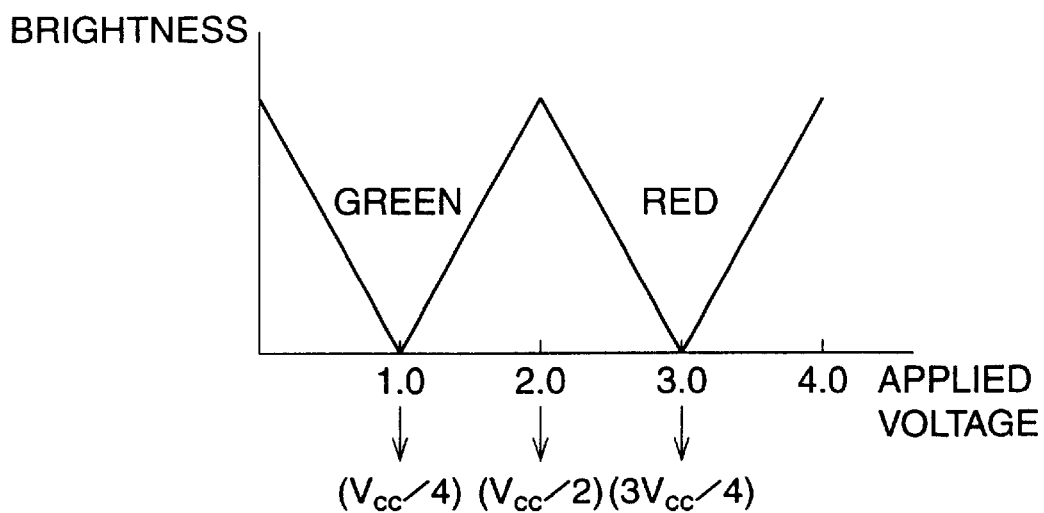
FIG. 12 is yet another graph representing the lighting control of an indicator lamp having a green LED and a red LED for indicating a level of adjusted voltage applied to the voltage-controlled amplifier.

As is apparent from the graph of FIG. 12, when the output voltage of the resistor ($68_1$, $68_2$) is at the zero level, the brightness of the green LED ($74G_1$, $74G_2$) is at the maximum level. As the output voltage of the resistor ($68_1$, $68_2$) is increased from the zero level toward the first reference voltage ($V_{cc}/4$), the brightness of the lit green LED ($74G_1$, $74G_2$) is gradually reduced toward the minimum level. When the output voltage of the resistor ($68_1$, $68_2$) reaches the first reference voltage ($V_{cc}/4$), the green LED ($74G_1$, $74G_2$) is turned OFF.

When the output voltage of the resistor ($68_1$, $68_2$) exceeds the first reference voltage ($V_{cc}/4$), the green LED ($74G_1$, $74G_2$) is again lit. As the output voltage of the resistor ($68_1$, $68_2$) is increased from the first reference voltage ($V_{cc}/4$) toward the second reference voltage ($V_{cc}/2$), the brightness of the lit green LED ($74G_1$, $74G_2$) is gradually increased toward the maximum level.

As soon as the output voltage of the resistor ($68_1$, $68_2$) exceeds the second reference voltage ($V_{cc}/2$), the green LED ($74G_1$, $74G_2$) is turned OFF, and the red LED ($74R_1$, $74R_2$) is lit at the maximum level. As the output voltage of the resistor ($68_1$, $68_2$) is increased from the second reference voltage ($V_{cc}/2$) toward the third reference voltage ($3V_{cc}/4$), the brightness of the lit red LED ($74R_1$, $74R_2$) is gradually reduced toward the minimum level. When the output voltage of the resistor ($68_1$, $68_2$) reaches the third reference voltage ($3V_{cc}/4$), the red LED ($74R_1$, $74R_2$) is turned OFF.

When the output voltage of the resistor ($68_1$, $68_2$) exceeds the third reference voltage ($3V_{cc}/4$), the red LED ($74R_1$, $74R_2$) is again lit. As the output voltage of the resistor ($68_1$, $68_2$) is increased from the third reference voltage ($3V_{cc}/4$) toward the maximum voltage (4 volts), the brightness of the lit red LED ($74R_1$, $74R_2$) is gradually increased toward the maximum level.

Thus, while watching the indicator lamps ($72_1$, $72_2$), the maintenance person can suitably and properly regulate the peak-to-peak level of the synchronizing-signal component (SYNC1, SYNC2). Note, of course, it can be easily realized by those skilled in the art, that the first and second LED driver $76_1$ and $76_2$ are designed such that the lighting control of the green and red LED's ($74G_1$ and $74R_1$; $74G_2$ and $74R_2$) is performed as shown in the graph of FIG. 12.

Finally, it will be understood by those skilled in the art that the foregoing description is of preferred embodiments of the system, and that various changes and modifications may be made to the present invention without departing from the spirit and scope thereof.

The present disclosure relates to subject matters contained in Japanese Patent Applications No. 2000-006919 (filed on Jan. 14, 2000) which is expressly incorporated herein, by reference, in its entirety.

What is claimed is:

1. An electronic endoscope system including a scope having a solid-state image sensor provided at a distal end thereof to generate image-pixel signals, and an image-signal processing unit that produces a video signal based on the image-pixel signals, which system comprises:

an alteration system that alters a peak-to-peak level of a synchronizing-signal component of said video signal;

an manual setting system that manually operates said alteration system to perform the alteration of the peak-to-peak level of said synchronizing-signal component;

an indicator system that indicates a degree of the alteration of the peak-to-peak level of said synchronizing-signal component during the operation of said manual setting system; and an output terminal that outputs said synchronizing-signal component having the peak-to-peak level defined by said alteration system.

2. An electronic endoscope system as set forth in claim 1, wherein said manual setting system is provided in a housing of said image-signal processing unit so as to be accessible by a suitable manual tool.

3. An electronic endoscope system as set forth in claim 1, wherein said alteration system comprises a voltage-controlled amplifier, an amplification factor of which is regulated in accordance with a level of a voltage signal applied thereto, and said manual setting system comprises a variable resistor that adjusts the level of said voltage signal.

4. An electronic endoscope system as set forth in claim 1, wherein said indicator system includes an indicator lamp visually provided at a suitable location of a housing of said image-signal processing unit, and a lamp driver system that controls lighting of said indicator lamp in accordance with the degree of alteration of the peak-to-peak level of said synchronizing-signal component.

5. An electronic endoscope system as set forth in claim 4, wherein said indicator lamp includes at least two light-emitting sources, and said driver system controls not only turn-ON and turn-OFF of said light-emitting sources but also brightness of said light-emitting sources in accordance with the degree of the alteration of the peak-to-peak level of said synchronizing-signal component.

6. An electronic endoscope system as set forth in claim 5, wherein said respective light-emitting sources emit different monochromatic light.

7. An electronic endoscope system as set forth in claim 4, wherein said lamp driver system includes an ON/OFF switch element that controls supply of electrical power from said lamp driver system to said indicator lamp, and a timer system that turns OFF said ON/OFF switch element after a predetermined time is elapsed from a time at which said ON/OFF switch is turned ON.

8. An electronic endoscope system as set forth in claim 1, wherein said alteration system comprises a voltage-controlled amplifier, an amplification factor of which is regulated in accordance with a level of a voltage signal applied thereto, and said manual setting system comprises a variable resistor that adjusts the level of said voltage signal, said manual setting system being provided in a housing of said image-signal processing unit so as to be accessible by a suitable manual tool.

9. An electronic endoscope system as set forth in claim 8, wherein said indicator system includes an indicator lamp visually provided at a suitable location of the housing of said image-signal processing unit, and a lamp driver system that controls lighting of said indicator lamp in accordance with the degree of alteration of the peak-to-peak level of said synchronizing-signal component.

10. An electronic endoscope system as set forth in claim 9, wherein said indicator lamp includes at least two light-emitting sources, and said driver system controls not only turn-ON and turn-OFF of said light-emitting sources but also brightness of said light-emitting sources in accordance with the degree of alteration of the peak-to-peak level of said synchronizing-signal component.

11. An electronic endoscope system as set forth in claim 10, wherein said respective light-emitting sources emit different monochromatic light.

12. An electronic endoscope system as set forth in claim 9, wherein said lamp driver system includes a tool-detection system that detects whether access to said manual setting system by said manual tool is made, and said lamp driver system is allowed to feed electric power to said indicator lamp only when the access to said manual setting system by said manual tool is detected by said tool-detection system.

13. An electronic endoscope system as set forth in claim 12, wherein said lamp driver system further includes an ON/OFF switch element that controls the supply of the electrical power from said lamp driver system to said indicator lamp, and said ON/OFF switch is turned ON only when the access to said manual setting system by said manual tool is detected by said tool-detection system.

14. An electronic endoscope system as set forth in claim 1, wherein said manual setting system includes a portion which is manually operated by a suitable manual tool, and which is arranged such that the manual tool is operable without interfering with a signal cable extending from said output terminal.

* * * * *